US00PP25266P3

(12) United States Plant Patent
Stewart

(10) Patent No.: US PP25,266 P3
(45) Date of Patent: Jan. 27, 2015

(54) ***ANIGOZANTHOS* PLANT NAMED 'RAMBOTATION'**

(50) Latin Name: ***Anigozanthos* hybrid**
Varietal Denomination: Rambotation

(71) Applicant: Ian Angus Stewart, Somersby (AU)

(72) Inventor: Ian Angus Stewart, Somersby (AU)

(73) Assignee: Ramm Botanicals Holdings, Pty, Ltd. (AU)

( * ) Notice: Subject to any disclaimer, the term of this patent is extended or adjusted under 35 U.S.C. 154(b) by 150 days.

(21) Appl. No.: 13/815,094

(22) Filed: Jan. 30, 2013

(65) Prior Publication Data

US 2014/0215663 P1 Jul. 31, 2014

(51) Int. Cl.
*A01H 5/00* (2006.01)

(52) U.S. Cl.
USPC ..... Plt./362

(58) Field of Classification Search
USPC ..... Plt./362
See application file for complete search history.

*Primary Examiner* — Anne Grunberg
(74) *Attorney, Agent, or Firm* — Cassandra Bright

(57) ABSTRACT

A new and distinct *Anigozanthos* cultivar named 'Rambotation' is disclosed, characterized red flowers, large quantity of flowers, short plant height and a long flowering season. The new variety is an *Anigozanthos*, normally produced as an outdoor garden or container plant.

2 Drawing Sheets

Latin name of the genus and species: *Anigozanthos* hybrid.
Variety denomination: 'Rambotation'.

BACKGROUND OF THE INVENTION

The new *Anigozanthos* cultivar is a product of a planned breeding program conducted by the inventor, Ian Angus Stewart, in Kangy Angy, Australia. The objective of the breeding program was to produce new *Anigozanthos* varieties for ornamental commercial applications. The cross resulting in this new variety was made Sep. 15, 2004.

Records of the specific parent varieties have been lost. The inventor is unable to supply names of or comparisons to the parent varieties. The new variety was discovered Sep. 19, 2007, by the inventor in a group of seedlings resulting from the September 2004 crossing, in a research greenhouse in Kangy Angy, Australia.

Asexual reproduction of the new cultivar was performed by tissue culture. This was first performed at a laboratory in Kangy Angy, Australia during 2007 and has shown that the unique features of this cultivar are stable and reproduced true to type over several successive generations.

SUMMARY OF THE INVENTION

The cultivar 'Rambotation' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Rambotation'. These characteristics in combination distinguish 'Rambotation' as a new and distinct *Anigozanthos* cultivar:

1. Short plant height
2. Large quantity of inflorescences

3. Red flowers
4. Long flowering season

COMMERCIAL COMPARISON

Plants of the new cultivar 'Rambotation' are comparable to the variety *Anigozanthos* 'Ramboball' U.S. Plant Pat. No. 20,271. The two *Anigozanthos* varieties are similar in most horticultural characteristics; however, the new variety 'Rambotation' differs in having longer foliage than 'Ramboball'. Additionally, plants of 'Rambotation' are taller than Ramboball and produce flowers with longer and wider perianth tubes than those of 'Ramboball'. Plants of 'Rambotation' produce inflorescence with primary ramification whereas inflorescences found on plants of 'Ramboball' have secondary ramification.

Plants of the new cultivar 'Rambotation' can also be compared to the commercial variety *Anigozanthos* 'Bush Ranger', U.S. Plant Pat. No. 6,478. These varieties are similar in most horticultural characteristics; however 'Bush Ranger' produces foliage with an erect aspect, whereas 'Rambotation' foliage is semi-erect. Additionally, plants of 'Rambotation' produce flowers with longer and wider perianth tubes than 'Bush Ranger'. Plants of 'Rambotation' produce inflorescence with less flower per inflorescence than 'Bush Ranger', and produce flowers with perianth tube pubescence of a different color.

BRIEF DESCRIPTION OF THE PHOTOGRAPHS

Figure 1:
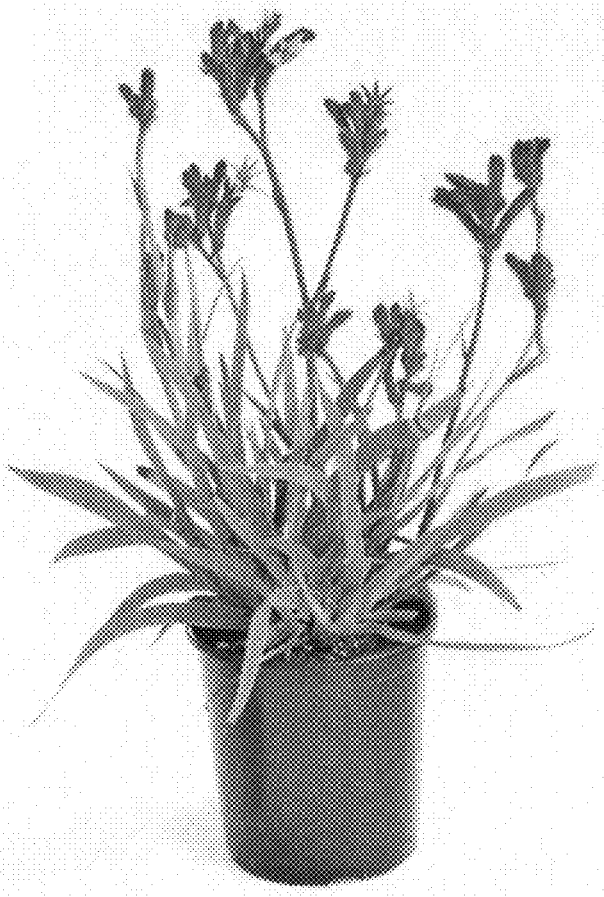

The accompanying photograph in FIG. 1 illustrates in full color a typical plant of 'Rambotation' grown in a greenhouse, in a 15 cm pot. Age of the plant photographed is approximately 1 year from a rooted plantlet.

Figure 2:
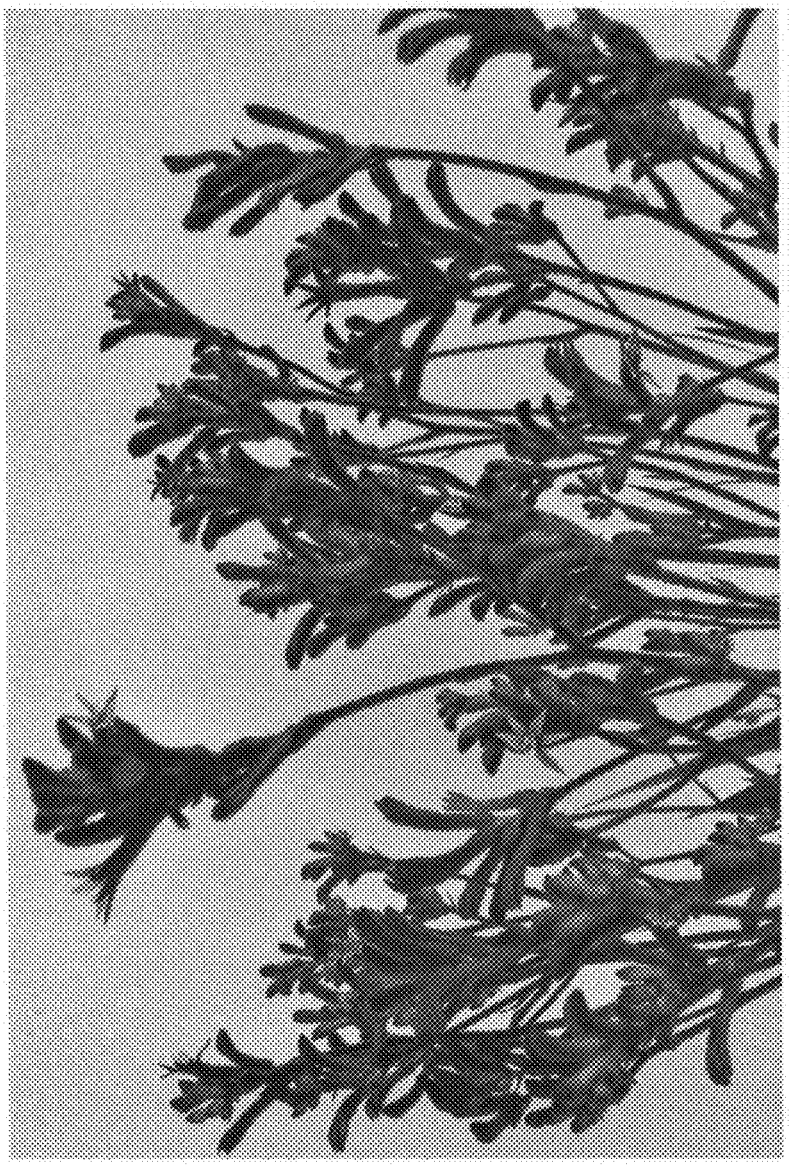

FIG. 2 illustrates in full color a close up of a typical bloom of 'Rambotation'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Rambotation' plants grown in a greenhouse, in Santa Paula, Calif. The growing temperature ranged from 20° C. to 35° C. during the day and from 17° C. to 23° C. during the night. General light conditions are bright, normal sunlight. Measurements and numerical values represent averages of typical plant types.

Botanical classification: *Anigozanthos* hybrid 'Rambotation'.

PROPAGATION

Typically propagated by micropropagation tissue culture. A tissue culture plantlet is typically rooted in 1 to 2 weeks at approximately 25° C.

Root description: Root description: Thick, fleshy main roots with fibrous network of much smaller roots.

PLANT

Age of plant described: Approximately 1 year from a rooted cutting.

Growth habit: Upright fan shaped perennial with basal only branching.

Pot size of plant described: Commercial 1 quarter size container.

Height:

*Top of foliar plane.*—30 to 38 cm.

Top of flowering plane.—55 to 70 cm.

Plant spread: 40 to 45 cm.

Growth rate: Moderate.

FOLIAGE

Leaf:

*Arrangement.*—Basally emerging, irregular rosette. Primarily fan-shaped.

*Quantity.*—Approximately 25 leaves on a 1 year old plant

*Average length.*—Approximately 30 cm.

*Average width.*—Approximately 1.8 cm.

*Shape of blade.*—Subulate.

*Apex.*—Acuminate.

*Base.*—Clasping

*Attachment.*—Sessile.

*Margin.*—Entire.

*Texture of top surface.*—Glabrous, ridged.

*Texture of lower surface.*—Glabrous, ridged.

*Color.*—Young foliage upper side: Near RHS Green 137B. Young foliage under side: Near RHS Green 137B. Mature foliage upper side: Near RHS Green 137B. Mature foliage under side: Near RHS Green 137B.

*Venation.*—Type: Pinnate. Venation color upper side: Near RHS Green 137B. Venation color under side: Near RHS Green 137B.

*Petiole.*—Not Present.

FLOWER

Natural flowering season: Freely flowering under outdoors growing conditions with substantially continuous blooming from spring through autumn.

Inflorescence and flower type and habit: Large flowers arranged singly on terminal and axillary racemes. Inflorescence have primary ramification. Individual flowers are zygomorphic, tubular, with a curved perianth.

Inflorescence height: Approximately 18 cm.

Inflorescence width: Approximately 11 cm.

Flower longevity on plant: Individual flowers last approximately 30 days.

Approximate quantity of flowers per plant: About 70 flowers and buds per plant. Average 12 to 15 flowers per inflorescence.

Persistent or self-cleaning: Persistent.

Bud:

*Shape.*—Tubular.

*Length.*—About 3.5 cm.

*Diameter.*—About 0.7 cm.

*Texture.*—Pilous.

*Color.*—Near RHS Red 45A, darker at tip, near Red 53A.

Flower size:

*Diameter.*—Approximately 1.8 cm.

*Length.*—Approximately 4.0 cm.

Petals (unfused floral section):

*Length.*—Approximately 1.1 cm.

*Diameter.*—Approxiately 0.7 cm.

*Quantity.*—4 or 5.

*Texture.*—Covered in dense, pilous hairs. Hairs colored near Red 53A.

*Apex.*—Acute.

*Color.*—When opening: Outer, visible surface: Near RHS Red 45A. Fully opened: Outer surface: Near RHS Red 53A. Inner surface: Near RHS Green-Yellow 1B. Fading: Outer surface: Near RHS Orange-Red N34A. Inner surface: Near RHS Yellow-Orange 17B.

Perianth tube:

*Length.*—Approximately 3.2 cm.

*Diameter.*—Approxiately 1.1 cm

*Texture.*—Outer texture highly pubescent, inner texture glabrous.

*Color.*—When opening: Outer, visible surface: Near RHS Red 53A. Fully opened: Outer surface: Near RHS Red 46A. Fading: Outer surface: Near RHS Yellow-Orange 17A.

Floral bracts:

*Quantity.*—1 at the base of each flower, or every other flower on inflorescence.

*Shape.*—Subulate.

*Tip.*—Cirrous.

*Base.*—Clasping.

*Texture.*—Heavily pilous.

*Length.*—Approximately 0.7 cm.

*Width.*—Approximately 0.2 cm.

*Color.*—Upper surface: Near RHS RHS Green-Yellow 1A. Lower surface: Near RHS Green-Yellow 1B.

Peduncle:
*Length*.—Average 40 cm.
*Diameter*.—0.7 cm.
*Color*.—Near RHS Orange-Red N34A.
*Aspect*.—Straight to slightly undulating.
*Strength*.—Very strong.
*Texture*.—Farinose and pilous.
Pedicels:
*Length*.—Average 0.2 cm.
*Diameter*.—0.1 cm.
*Color*.—Near RHS Orange-Red N34A.
*Orientation*.—Approximately 45 degrees from peduncle.
*Strength*.—Very strong.
*Texture*.—Pilous.
Sepals not present.
Fragrance: None.

REPRODUCTIVE ORGANS

Stamens:
*Number*.—6.
*Filament length*.—Filaments are mostly fused to petals. Approximately 0.4 cm, unfused.
*Filament color*.—Near RHS Green-Yellow 1B.
Anthers:
*Shape*.—Ovoid.
*Length*.—Approximately 0.1 cm.
*Color*.—Near RHS Orange-Red N34A.
*Pollen*.—Not observed.
Pistil:
*Number*.—1.
*Length*.—Approximately 3 cm.
*Style*.—Length: Approximately 3.1 cm. Color: Near RHS White 155D.
*Stigma*.—Shape: Linear. Length: Approximately 0.1 cm. Color: Near RHS Orange-Red N34A. Ovary Color: RHS Yellow 7A.

OTHER CHARACTERISTICS

Seeds and fruits: Not observed to date.
Disease/pest resistance: Common to cultivar.
Temperature tolerance: From approximately 0° C. to more than 40° C.

What is claimed is:

1. A new and distinct cultivar of *Anigozanthos* plant named 'Rambotation' as herein illustrated and described.

* * * * *